(12) United States Patent
Kamler

(10) Patent No.: US 9,693,778 B2
(45) Date of Patent: Jul. 4, 2017

(54) BANDING APPARATUS AND METHOD OF USE

(71) Applicant: Alpine Medical Devices, LLC, Carmel, CA (US)

(72) Inventor: Jan P. Kamler, Reno, NV (US)

(73) Assignee: Alpine Medical Devices, LLC, Carmel, CA (US)

( * ) Notice: Subject to any disclaimer, the term of this patent is extended or adjusted under 35 U.S.C. 154(b) by 118 days.

(21) Appl. No.: 13/779,576

(22) Filed: Feb. 27, 2013

(65) Prior Publication Data

US 2013/0226198 A1    Aug. 29, 2013

Related U.S. Application Data

(60) Provisional application No. 61/603,839, filed on Feb. 27, 2012.

(51) Int. Cl.
*A61B 17/10* (2006.01)
*A61B 17/12* (2006.01)
*A61B 17/30* (2006.01)

(52) U.S. Cl.
CPC ........ *A61B 17/12013* (2013.01); *A61B 17/12* (2013.01); *A61B 17/12009* (2013.01); *A61B 2017/306* (2013.01)

(58) Field of Classification Search
CPC .......... A61B 17/12; A61B 2017/12018; A61B 17/12009; A61F 17/12
See application file for complete search history.

(56) References Cited

U.S. PATENT DOCUMENTS 3,760,810 A * 9/1973 Van Hoorn ...... A61B 17/12013
                                                       606/140
3,967,625 A * 7/1976 Yoon ................ A61B 17/12013
                                                       128/831
(Continued)

FOREIGN PATENT DOCUMENTS

CN          86203090 U     4/1987
CN           2036031 U     4/1989
(Continued)

OTHER PUBLICATIONS

Wikipedia; Endoscopy; 7 pgs.; retrieved from the internet Sep. 28, 2012 (http://en.wikipedia.org/wiki/Endoscopy).
(Continued)

*Primary Examiner* — Richard Louis
(74) *Attorney, Agent, or Firm* — Shay Glenn LLP

(57) ABSTRACT

A banding apparatus and method. One embodiment is a unitary or integrated hemorrhoidal single hand-held and single hand-operated ligator, which can, in some embodiments, enable direct visualization and release of multiple bands. The ligator has a gun-shaped handle extending from a vacuum generating trigger tube, with a fixed band bearing barrel extending from the vacuum generating trigger tube. A vacuum generating tube extends through the band bearing barrel from the rear of the gun ligator to the band bearing barrel end of the ligator gun, and is in air movement communication with the vacuum generating tube and band bearing barrel end of the ligator gun. A band actuating barrel is threadably mounted to surround a portion of the band bearing barrel, and rotation of the barrel cause the barrel to move laterally and force one or more ligating bands along and off of the band bearing barrel end. A light source can be included to illuminate the band bearing barrel end. Most components are made of nearly transparent. durable, lightweight, recyclable plastic, such as polypropylene; and with (Continued)

such components the operator can see through the gun components and observe the material, such as a hemorrhoid, to be ligated.

17 Claims, 14 Drawing Sheets

(56) References Cited

U.S. PATENT DOCUMENTS

| | | | |
|---|---|---|---|
| 4,226,239 A | 10/1980 | Polk et al. | |
| 4,735,194 A * | 4/1988 | Stiegmann | A61B 1/015 600/104 |
| 5,203,863 A * | 4/1993 | Bidoia | A61B 1/31 604/902 |
| 5,320,630 A | 6/1994 | Ahmed | |
| 5,356,416 A | 10/1994 | Chu et al. | |
| 5,462,559 A | 10/1995 | Ahmed | |
| 5,507,797 A * | 4/1996 | Suzuki | A61B 17/12013 606/139 |
| 5,569,268 A | 10/1996 | Hosoda | |
| 5,624,453 A | 4/1997 | Ahmed | |
| 5,643,293 A | 7/1997 | Kogasaka et al. | |
| 5,735,861 A | 4/1998 | Peifer et al. | |
| 5,741,273 A | 4/1998 | O'Regan | |
| 5,788,715 A | 8/1998 | Watson et al. | |
| 6,007,551 A | 12/1999 | Peifer et al. | |
| 6,059,719 A | 5/2000 | Yamamoto et al. | |
| 6,136,009 A | 10/2000 | Mears | |
| 6,235,040 B1 | 5/2001 | Chu et al. | |
| 6,547,798 B1 | 4/2003 | Yoon et al. | |
| 6,610,072 B1 | 8/2003 | Christy et al. | |
| 6,685,713 B1 | 2/2004 | Ahmed | |
| 6,923,756 B2 | 8/2005 | Sudakov et al. | |
| 7,037,314 B2 | 5/2006 | Armstrong | |
| 7,189,247 B1 | 3/2007 | Zirps et al. | |
| 8,062,308 B2 | 11/2011 | Noda et al. | |
| 8,974,474 B2 | 3/2015 | Kamler | |
| 2002/0026199 A1 * | 2/2002 | Fortier | A61B 17/00234 606/108 |
| 2002/0072757 A1 * | 6/2002 | Ahmed | A61B 17/12013 606/139 |
| 2003/0009086 A1 * | 1/2003 | Black | A61B 1/00039 600/168 |
| 2004/0006256 A1 | 1/2004 | Suzuki et al. | |
| 2005/0277955 A1 | 12/2005 | Palmer et al. | |
| 2006/0058816 A1 | 3/2006 | Hassanien | |
| 2006/0089660 A1 | 4/2006 | Saeed et al. | |
| 2006/0122632 A1 | 6/2006 | Hassanien et al. | |
| 2006/0161170 A1 * | 7/2006 | DeLuca et al. | 606/106 |
| 2006/0259041 A1 * | 11/2006 | Hoffman | A61B 17/12013 606/139 |
| 2007/0093855 A1 | 4/2007 | Zhang | |
| 2007/0118162 A1 | 5/2007 | Abi Kheirs | |
| 2008/0004622 A1 | 1/2008 | Coe et al. | |
| 2008/0009668 A1 * | 1/2008 | Cohn | A61B 17/32 600/37 |
| 2008/0255412 A1 * | 10/2008 | Surti | A61B 17/12013 600/104 |
| 2008/0287965 A1 | 11/2008 | Ducharme | |
| 2009/0131748 A1 | 5/2009 | Chami | |
| 2009/0198255 A1 | 8/2009 | Ikeda | |
| 2010/0063517 A1 * | 3/2010 | Cleator | A61B 17/12013 606/140 |
| 2011/0077666 A1 | 3/2011 | McCahon et al. | |
| 2012/0078272 A1 | 3/2012 | Smith | |
| 2015/0173766 A1 | 6/2015 | Kamler | |

FOREIGN PATENT DOCUMENTS

| | | | |
|---|---|---|---|
| CN | 2332365 Y | 8/1999 | |
| CN | 2596947 Y | 1/2004 | |
| CN | 201067419 Y | 6/2008 | |
| CN | 201067420 Y | 6/2008 | |
| EP | 1147744 A2 | 10/2001 | |
| EP | 1077648 | 11/2005 | |
| GB | 1334560 A | 10/1973 | |
| GB | 2426459 A | 11/2006 | |
| IE | WO 9965400 A1 * | 12/1999 | A61B 17/12013 |
| JP | 04312745 B2 | 8/2009 | |
| WO | WO96/24292 A1 | 8/1996 | |
| WO | WO9965400 | 12/1999 | |
| WO | WO 9965400 A1 * | 12/1999 | |
| WO | WO 2004/021865 | 3/2004 | |
| WO | WO2004/021865 A2 | 3/2004 | |
| WO | WO2007079674 | 7/2007 | |
| WO | WO 2009/144694 | 12/2009 | |
| WO | WO2009/144694 A1 | 12/2009 | |
| WO | WO2010028486 | 3/2010 | |

OTHER PUBLICATIONS

International Search Report and Written Opinion of the International Searching Authority for International Application PCT/US2013/28085, mailed May 6, 2013.

* cited by examiner

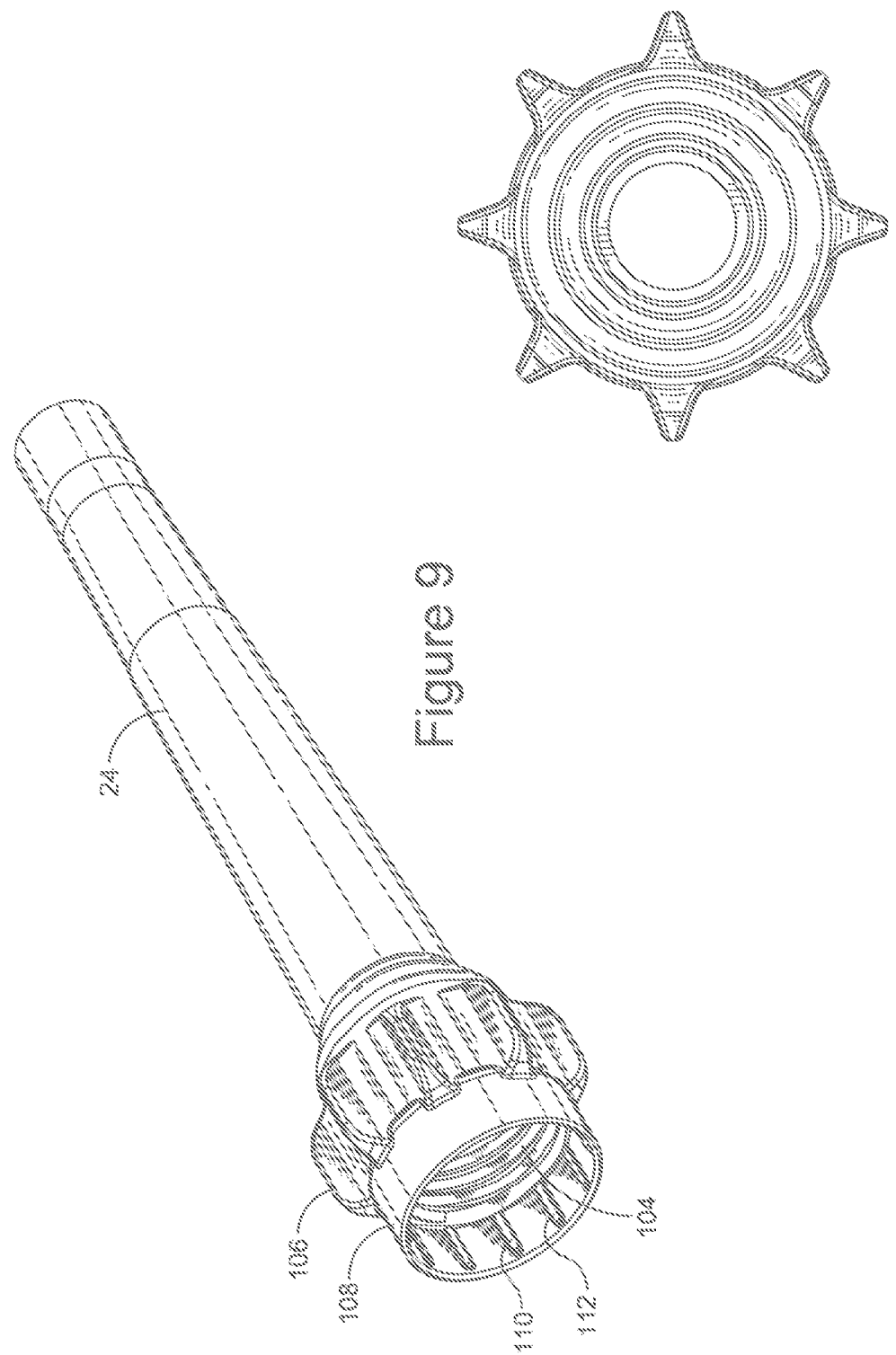

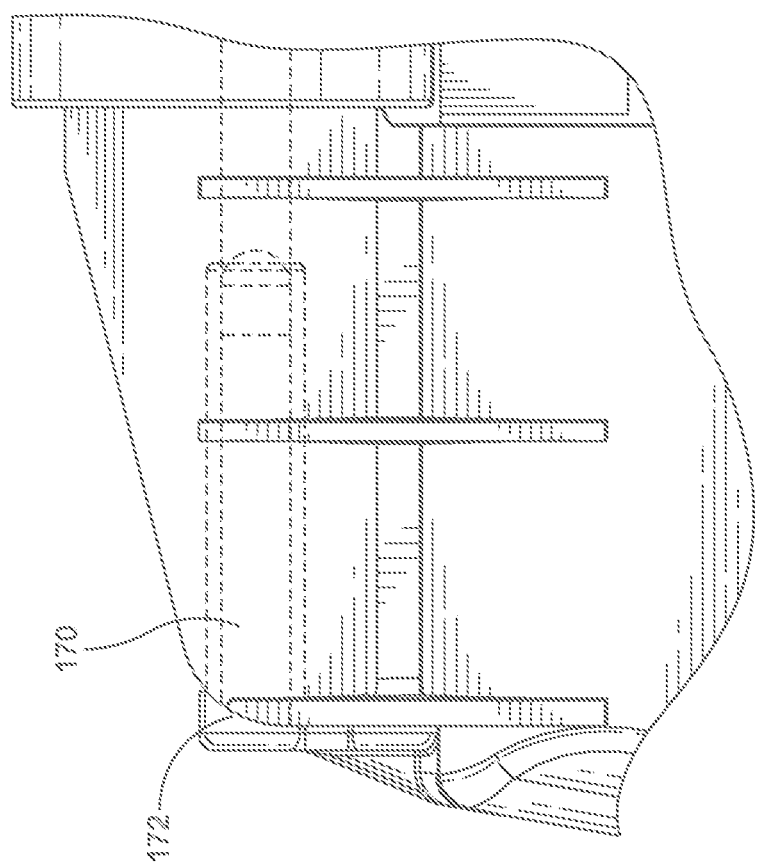

BANDING APPARATUS AND METHOD OF USE

CROSS-REFERENCE TO RELATED APPLICATION

The present nonprovisional application claims priority through Applicant's prior provisional patent application of the same title, Ser. No. 61/603,839, filed Feb. 27, 2012, which prior provisional patent application is hereby incorporated by reference in its entirety. In the event of any inconsistency between such prior provisional patent application and the present nonprovisional application, the present nonprovisional application shall prevail.

TECHNICAL FIELD

The present disclosure is directed to a banding apparatus and method of banding, and in one particular embodiment, to a hemorrhoid ligator and method of hemorrhoidal ligation.

BACKGROUND

The process of ligation of internal hemorrhoids is decades old. The principal of ligation is strangulation of redundant hemorrhoidal tissue. This is achieved by placing a rubber band (a "ligature") over hemorrhoidal tissue that is pinched or suctioned into an open tube.

One such prior art ligator is used with an endoscope. This type of ligator is attached to the tip of the endoscope, introduced into the rectum, and retroflexed toward one or more hemorrhoids to be ligated. The one or more hemorrhoids are suctioned into the ligator, and the ligator then applies ligating bands to each such hemorrhoid. This endoscope-based procedure allows the operator to directly visualize the hemorrhoid before and during the ligation process; but this endoscopic process is complex, requires extensive training, and requires use of an expensive endoscope in an endoscopy unit or operating room setting.

Similar and other ligators have been in use for many years to treat symptomatic internal hemorrhoids in outpatient ambulatory gastroenterology (GI) or surgical practices. These devices include the CRH O'Reagon Disposable Ligator made by CRH Medical, the Short-Shot Saeed Hemorrhoidal Multi-Band Ligator by made by Wilson Cook Medical, and the Haemoband made by Haemoband Surgical Ltd.

The CRH O'Regan procedure includes use of an anoscope to identify the location of internal hemorrhoids. If hemorrhoids are found, the anoscope is removed and a single band is loaded onto the tip of the ligator. The ligator is blindly inserted into the rectum. The tip of the ligator is then directed toward the location of a previously identified hemorrhoidal column. While holding the ligator with one hand, suction is applied with the other hand and tissue is pulled into the ligator, and the ligating band is deployed by sliding an overtube over the end of the ligator. If more banding is needed, then the ligator must be removed and re-loaded with another band. While this CRH technique allows for hand-applied suctioning and lower cost than endoscope-based techniques, this technique requires repeated instrumentation of the anus, blind ligation, application of only a single band during a given insertion of the ligator, and difficult reloading of bands on the tip of the device.

The Short-Shot Ligator is a hand-held instrument with capacity for up to four preloaded bands. After insertion of an anoscope, and identification of hemorrhoids, the anoscope is left in place and the ligator is pushed through the anoscope. The tip of the ligator is then approximated to the tissue, which is suctioned into the ligator using an external suctioning system. The bands are then deployed by using a string mechanism manipulated by the thumb. While this technique allows deployment of multiple, preloaded bands in a single insertion of the ligator, it requires use of an external suctioning system not available outside of an endoscopic or surgical setting. This procedure also provides only semi-direct visualization. While the anoscope is in place, target hemorrhoidal tissue can be seen only until the ligator is introduced into the anoscope. At that point, direct visualization is lost and the ligation procedure requires that the practitioner approximate the tip of the ligator to the target hemorrhoid blindly (meaning that the practitioner tries to put the tip where the practitioner remembers the hemorrhoids to be in the prior inspection). This approximation may be inaccurate and does not allow direct visualization of the amount of suctioned hemorrhoidal tissue. This may lead to suctioning of a small amount of hemorrhoidal tissue leading to limited success of the procedure.

The Haemoband Ligator is similar to the Short Shot but differs in that it can deploy multiple preloaded bands by a hand-trigger mechanism. This ligator is used in conjunction with a lighted anoscope. Use of the anoscope and approximation of the tip of the ligator is identical to the Short-Shot Ligator, resulting in the same issues described above for the Short-Shot Ligator.

BRIEF SUMMARY OF CERTAIN ASPECTS OF THIS SPECIFICATION

The applicant has invented a banding apparatus and banding method having a substantial number of aspects. In one banding method aspect, the operator can grip the actuator with one hand and while holding the actuator with the one hand: with the one hand actuate the ligator to remove air from a vacuum generating portion of the ligator; insert one end of the ligator into a cavity of a human or other living entity; observe target material, such as target flesh, through the ligator during the ligation process; with the one hand actuate the ligator to generate a vacuum and suck the target material into the ligator with the vacuum; and with the same hand actuate the ligator to release a ligating band around the sucked-in material.

In another aspect, the operator observes the target material through the material sucking structure. In yet another aspect, the operator can use an additional structure, such as an anoscope for example, to first locate the target material, and the operator can then insert the sucking portion of the ligator through the additional locating structure about material to be ligated. In a further aspect, the target material is a hemorrhoid, and in yet another, the ligator can carry and release multiple ligating bands during one instrument penetration of the applicable cavity.

In another aspect, the one hand can actuate the ligator to generate a vacuum with a trigger on the ligator. In a still further aspect, the one hand can actuate the ligator to release the ligating band with a finger rotating an actuation tab on the ligator.

In another aspect, during a single penetration of the cavity, the ligator can be moved one or more times to allow the operator to observe through the ligator, and apply a ligating band, to other target material, such as a target hemorrhoid as an example. In a further aspect, the ligator can be used only one time and then thrown away. In yet another aspect, the ligator can be sterilized and reused.

Certain embodiments of the ligator apparatus include a vacuum drawing barrel, a narrower vacuum drawing tube or section within the barrel, and a band actuating barrel surrounding the vacuum drawing barrel. Some embodiments include an enlarged vacuum drawing section in air transport communication with the narrower vacuum drawing tube or section. In certain instances, the internal volume of the enlarged vacuum drawing tube or section is substantially larger than the combined volume of narrower vacuum drawing tube or section and any additional vacuum drawing portions of the ligator.

Some embodiments of the enlarged vacuum drawing tube or section include a sealed trigger penetrating the tube or section, and in certain instances, the sealed trigger is biased towards a decompressed or unactuated position.

In some ligators, the band actuating barrel surrounds the vacuum drawing barrel. The band actuating barrel can be actuated to slide and eject one ore more ligating bands mounted about the band ligating end of the vacuum drawing barrel. The band actuating barrel of some embodiments is threadably mounted to the vacuum drawing barrel and is finger rotatable to move the band actuating barrel to eject one or more ligating bands.

In certain instances, the vacuum drawing barrel is somewhat transparent or translucent. Some instances include a somewhat transparent or translucent band actuating barrel and vacuum drawing tube or section within the interior of at least a portion of the vacuum drawing barrel.

One embodiment of the ligator is hand holdable and includes a vacuum actuating trigger activatable with the one hand and a band actuating barrel actuatable with the same hand. Some embodiments provide a unitary, hand-held ligator including a vacuum drawing barrel, a band actuating barrel, an enlarged vacuum drawing section in vacuum drawing communication with the vacuum drawing barrel, and a vacuum drawing trigger. In some embodiments, the unitary ligator includes a hand-actuatable structure to actuate the band actuating barrel. In some instances, the band ejection end of the ligator is insertable into a cavity, and the vacuum-drawing trigger and hand-actuatable structure are activatable by a finger.

In some ligator embodiments, the hand-actuatable structure can include inwardly extending tabs on the band actuating barrel and outwardly extending tabs of the vacuum drawing barrel. These tabs can interact as the band actuating barrel moves, limiting movement of the band actuating barrel until sufficient force is applied to overcome resistance to barrel movement provided by the interacting tabs.

Some embodiments of the ligator can be made of lightweight yet rigid material, such as a rigid plastic, for many of the components.

Some embodiments have a unitary gun-shape, with a handle and trigger extending a nearly transparent or translucent rigid vacuum-generating and ligature-delivery tube. This and other ligator embodiments can be particularly durable, easy to use with one hand, and economical, and have a long shelf-life. They can be made of dominantly recyclable materials as well, such as steel and recyclable plastic.

There are other aspects and advantages of the present apparatus and methods disclosed by the present specification. They will become apparent as the specification proceeds. In this regard, it is to be understood that the Background and this Brief Summary are not intended to be limiting, and thus the scope of the invention is to be determined by the claims as issued and not whether given subject matter addresses an issue noted in the Background or includes subject matter recited in this Brief Summary.

BRIEF DESCRIPTION OF THE DRAWINGS

The applicant's preferred and other embodiments are further disclosed in association with the accompanying drawings, in which:

FIG. 9 is perspective view of the outer band ejection tube of FIG. 8;

FIG. 10 is front elevational view of the outer band ejection tube of FIG. 8;

FIG. 24 is a partial cross-sectional view of a ligator embodiment, taken along section line 24-24 of FIG. 5, having a removable battery and battery powered LED light source within the ligator to provide light at the ligating end of the ligator.

It is to be understood that spacially-orienting terms, such as top, bottom, front, back, upwardly, or downwardly are used to explain relative orientation of structures as shown in the Figures and as the structures might be used. They are not to be construed, however, to require such an orientation in space.

DETAILED DESCRIPTION

FIGS. 1-24 depict a ligator that can be utilized to ligate flesh such as one or more hemorrhoids. This ligator and the associated ligator components and methods can be used to ligate other material, human or otherwise.

Figure 1:
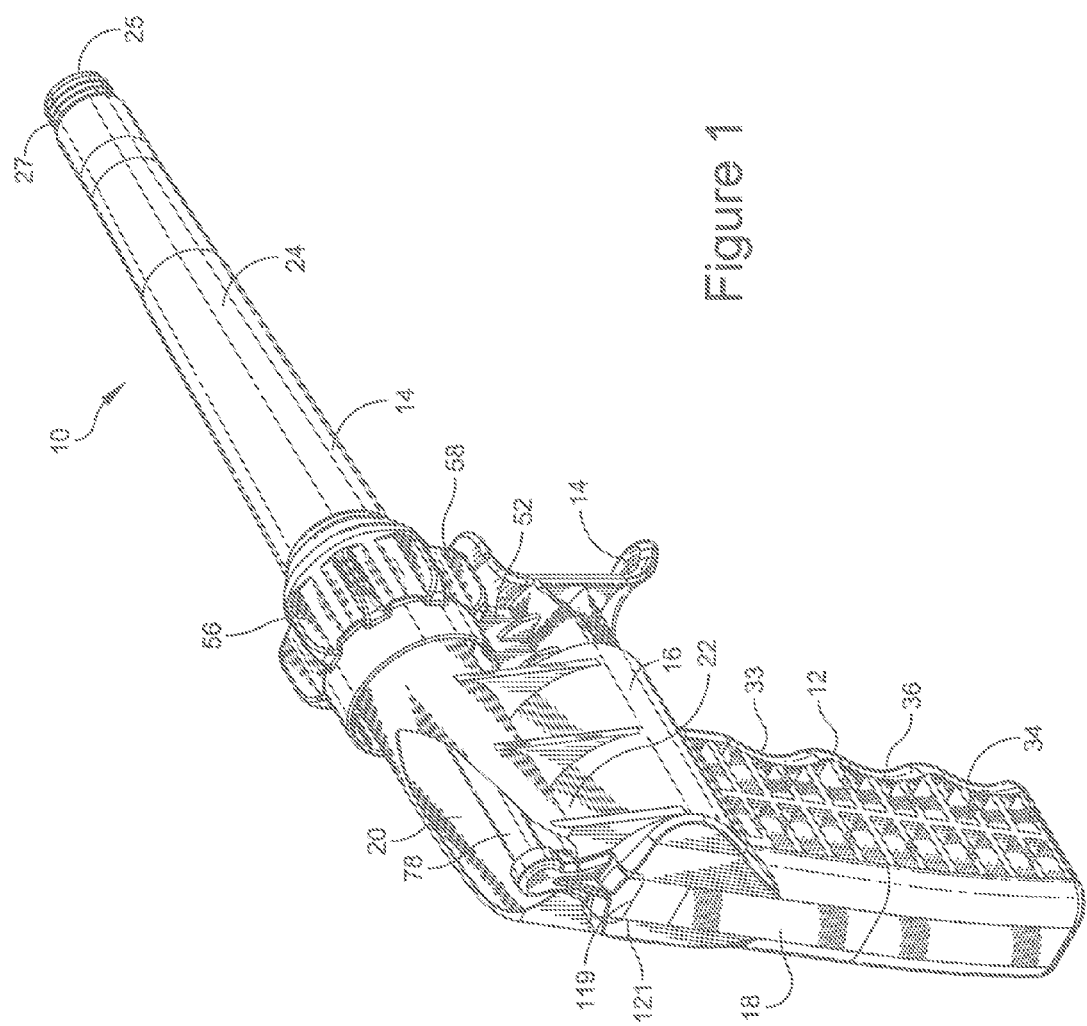
FIG. 1 is a perspective view of a unitary, hand-held banding ligator.

With reference now to FIG. 1, one embodiment of the present ligator, generally 10, is gun-shaped, having a handle 12, a vacuum drawing trigger 14 slidably penetrating a vacuum drawing tube 16 extending from the upper end 18 of the handle 12, and a fixed banding barrel 20 extending transversely from the upper side 22 of the vacuum drawing tube 16. An external banding barrel 24 slidably surrounds the central external periphery (not shown in FIG. 1) of the fixed banding barrel 20; and a band bearing tubular end 25 of the fixed banding barrel 20 extends outwardly from the tubular band ejecting end 27 of the external banding barrel 24. The external banding barrel 24 thus surrounds, and is coaxial with, the fixed banding barrel 20.

Figure 2:
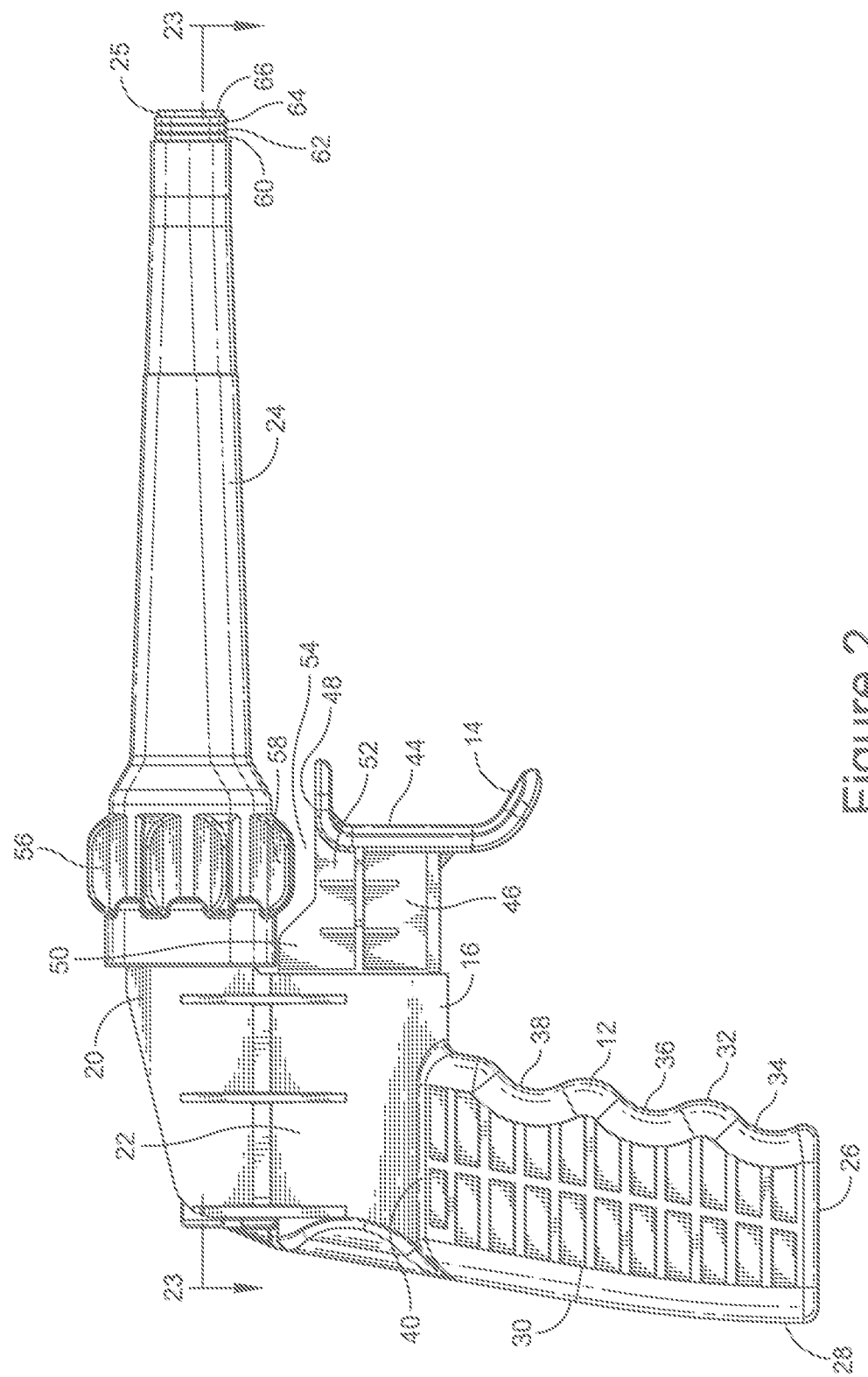
FIG. 2 is a right side elevational view of the banding ligator of FIG. 1.

With reference now to FIG. 2, the handle 12 has a generally planer bottom end 26 extending transversely from the lower end 28 of the back side 30 of the handle 12. The front side 32 of the handle 12 has three concave finger grip channels 34, 36, 38 extending along the front side 32 of the handle 12 from the bottom end 26 to the top end 40 of the handle 12.

The front side 44 of the vacuum drawing trigger 14 provides a somewhat contract finger trigger channel with a vacuum drawing tube plunger section 46 extending from the trigger channel 44 to penetrate the vacuum drawing tube 16. The top side 48 of the trigger channel 44 and the plunger section 46 extend angularly downwardly from a taller or deeper portion 50 of the tube plunger section 46. The relatively shallower section 52 of the tube plunger section 46 thus provides a free area 54 above the trigger 14 through which finger actuatable tabs, e.g., 56, 58, extending radially outwardly from the external banding barrel 24, can rotate with respect to the fixed banding barrel 20.

In this embodiment, the band bearing end 25 of the fixed banding barrel 20 has three ligation rubber bands 60, 62, 64 mounted in mating concave rubber band mounting channels (not shown) in the outer periphery band bearing end 25 (note that there is room 66 for a fourth band to be mounted at the periphery band bearing end 25 as shown in FIG. 2). Differing numbers of bands and mating mounting channels may be utilized; and concave mounting channels (or ribs) may also be eliminated if desired.

Figure 3:
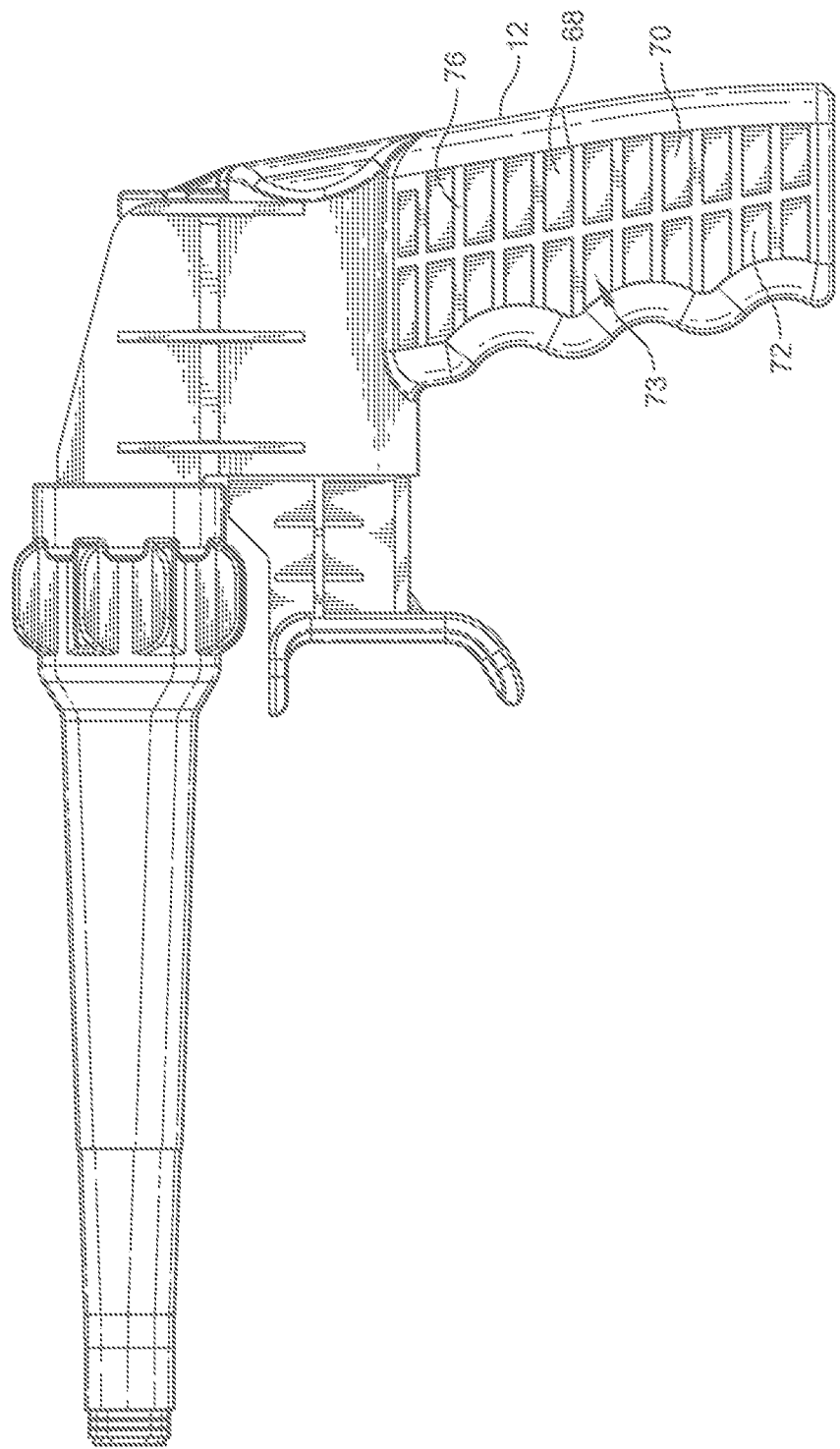
FIG. 3 is a left side elevational view of the banding ligator of FIG. 1.
Figure 8:
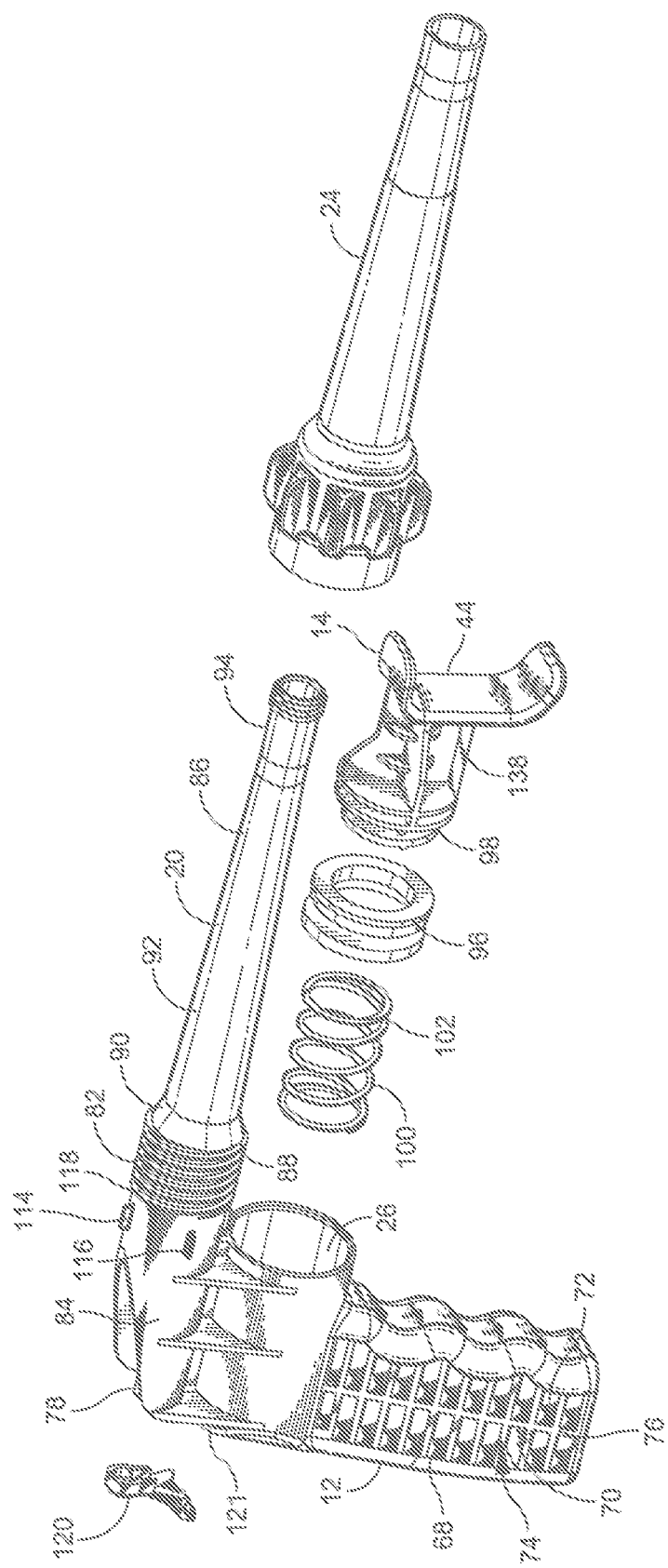
FIG. 8 is an exploded perspective view of the banding ligator of FIG. 1 having a main ligator body, a outer band ejection tube, a vacuum tube end plug, a trigger, a rubber plunger, and a spring.
Figure 13:
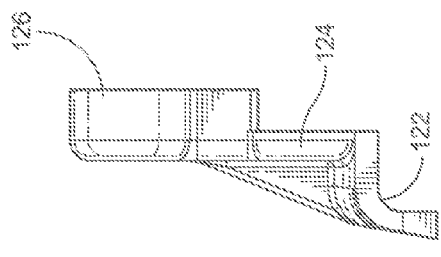
FIG. 13 is a right side elevational view of the plug of FIG. 8.

With reference now to FIGS. 3 and 8, the handle 12 also includes rectangular channels or passages, e.g., 68, 70, 72, passing through the handle 12 for the handle left side 74 to the handle right side 76. The resulting rectangular framing 73 extends from the handle left side 74 to the handle right side 76 to provide a rigid grippable handle surface on theses sides 74, 76 while reducing the amount of material in the handle 12.

Figure 5:
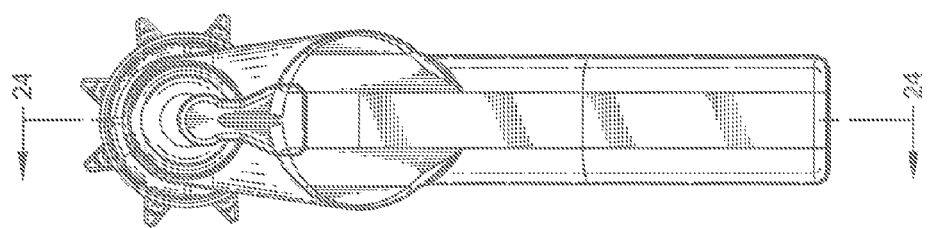
FIG. 5 is a back side elevational view of the banding ligator of FIG. 1.
Figure 4:
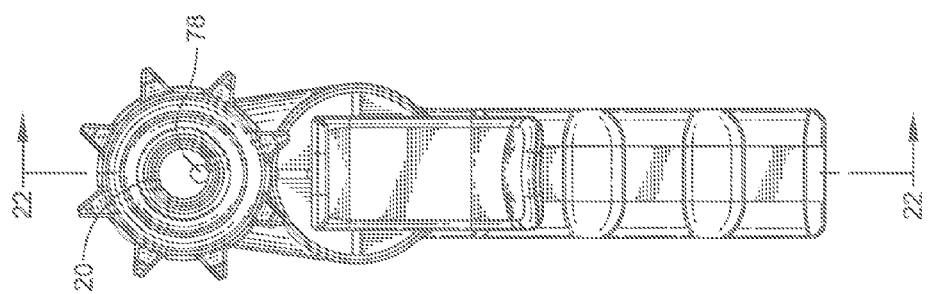
FIG. 4 is a front side elevational view of the banding ligator of FIG. 1.
Figure 6:
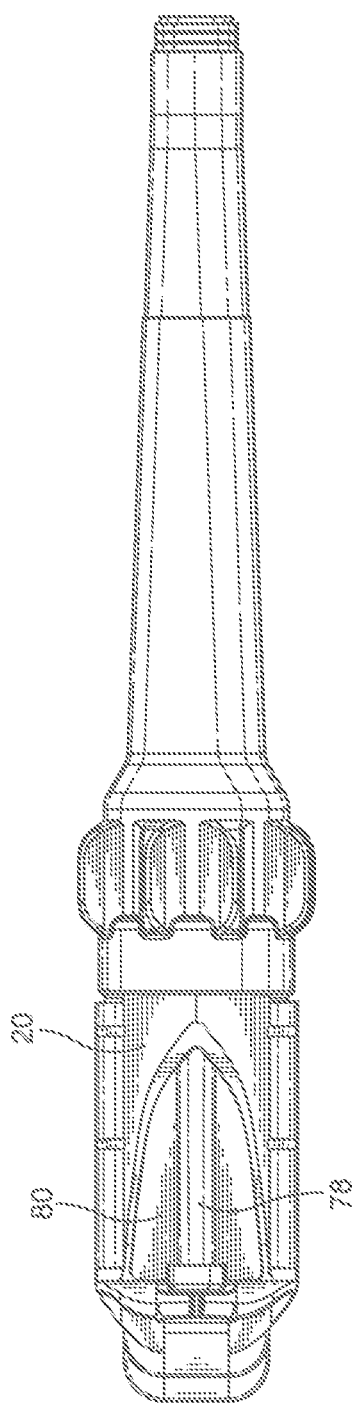
FIG. 6 is a top plan view of the banding ligator of FIG. 1.
Figure 7:
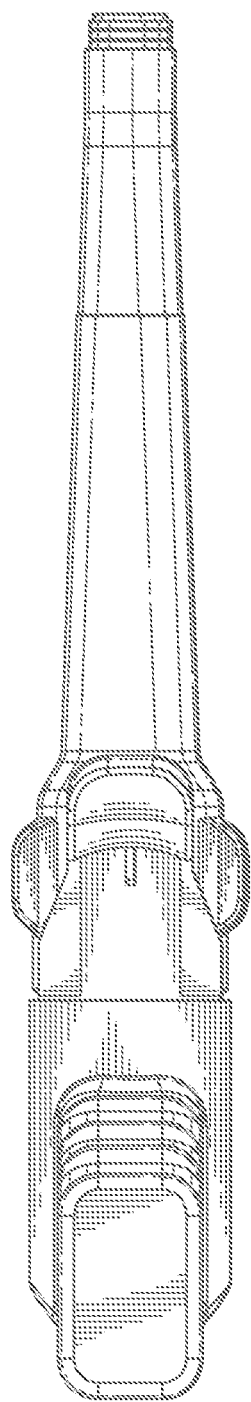
FIG. 7 is a bottom plan view of the banding ligator of FIG. 1.

With reference now to FIG. 4, the fixed banding barrel 20 includes an interior vacuum drawing barrel 78. With reference to FIGS. 5 and 6, this vacuum drawing barrel 78 extends to the back end 80 of the ligator gun 10.

With reference now to FIG. 8, the fixed banding barrel 20 includes an exterior threaded section 82 intermediate the back end 84 and front end 86 of the banding barrel 20. The forward end 88 of the threaded section 82 terminates in a narrowing conical neck, 90, which in turn terminates is a less steeply angled conical front barrel section 92. The conical front barrel section 92 in turn terminates in a banding tubular section 94, on which banding bands can be mounted. The external banding barrel has an interior periphery (not shown in FIG. 8) that generally mates with the external periphery of the fixed banding barrel 20.

The vacuum drawing trigger 14 has a rubber vacuum sealing plunger cap 96 that mounts on the cap mounting end 98 of the trigger 14 opposite its finger channel 44. The diametral width of the sealing cap 96 is slightly wider than the interior diameter of the vacuum drawing tube 16. A stainless steel spring 100 mounts within the interior of vacuum drawing tube 16 coaxially with the tube 16. The sealing cap 96 and trigger 14 mount with the sealing cap 96 friction fit within the interior of the vacuum drawing tube 16 to abut a forward end 102 of the spring 100. A sealing cap or plug 120 mounts within a mating plug mounting slot (see 119 in FIG. 1) in the back end 121 of the fixed banding barrel 20.

With reference now to FIG. 9, the exterior banding barrel 24 has an internal thread section 104 that threadably mates with, as shown in FIG. 8, the exterior threaded section 82 on the fixed banding barrel 20. Referring back to FIG. 9, the back end 106 of the interior threaded section 104 terminates in a generally tubular back end 108 of the exterior banding barrel 24. The tubular back end 108 has radially inwardly extending adjuster tabs, e.g., 110, 112, coaxial with the axis of the exterior banding barrel 24. These inwardly extending tabs, e.g., 110, 112, are sized to abut, as shown in FIG. 8, a portion of the side walls of similarly sized radially outwardly extending adjuster tabs, e.g., 114, 116, on the fixed banding barrel 14 adjacent the back end 118 of the threaded section 82 on the barrel 14.

With reference now to FIGS. 11, 12, 13, 14, and 15, the sealing plug 120 has an arced base 122, a sealing wall 124 extending upwardly from the arced base 122, and a tube sealing cap 126 extending from upper end 128 of the sealing wall 124 opposite the arced base 122.

Figure 16:
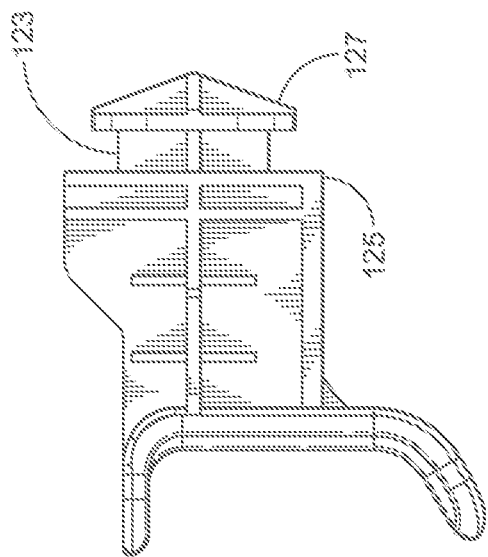
FIG. 16 is a left side elevational view of the trigger of FIG. 8.
Figure 18:
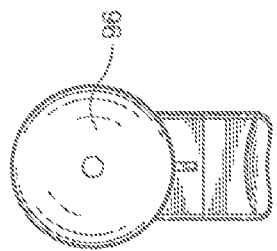
FIG. 18 is a back side elevational view of the trigger and plunger of FIG. 18.
Figure 21:
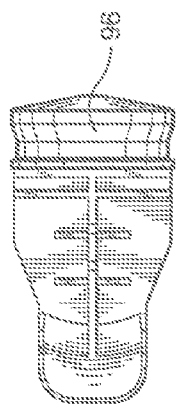
FIG. 21 is a top plan view of the trigger and plunger of FIG. 18.
Figure 17:
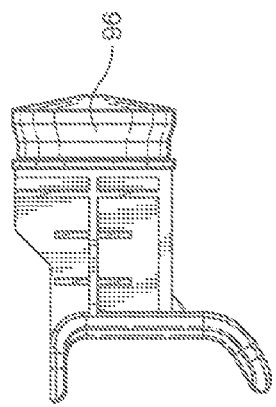
FIG. 17 is a left side elevational view of the trigger of FIG. 8 with the rubber plunger mounted on the back end of the trigger.
Figure 20:
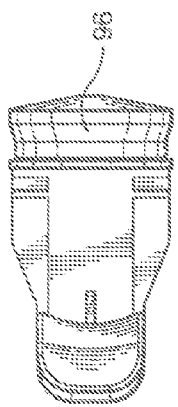
FIG. 20 is a bottom plan view of the trigger and plunger of FIG. 18.
Figure 19:
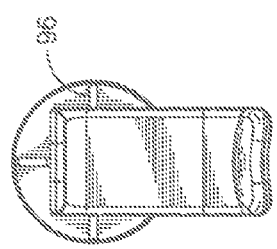
FIG. 19 is a front side elevational view of the trigger and plunger of FIG. 18.
Figure 22:
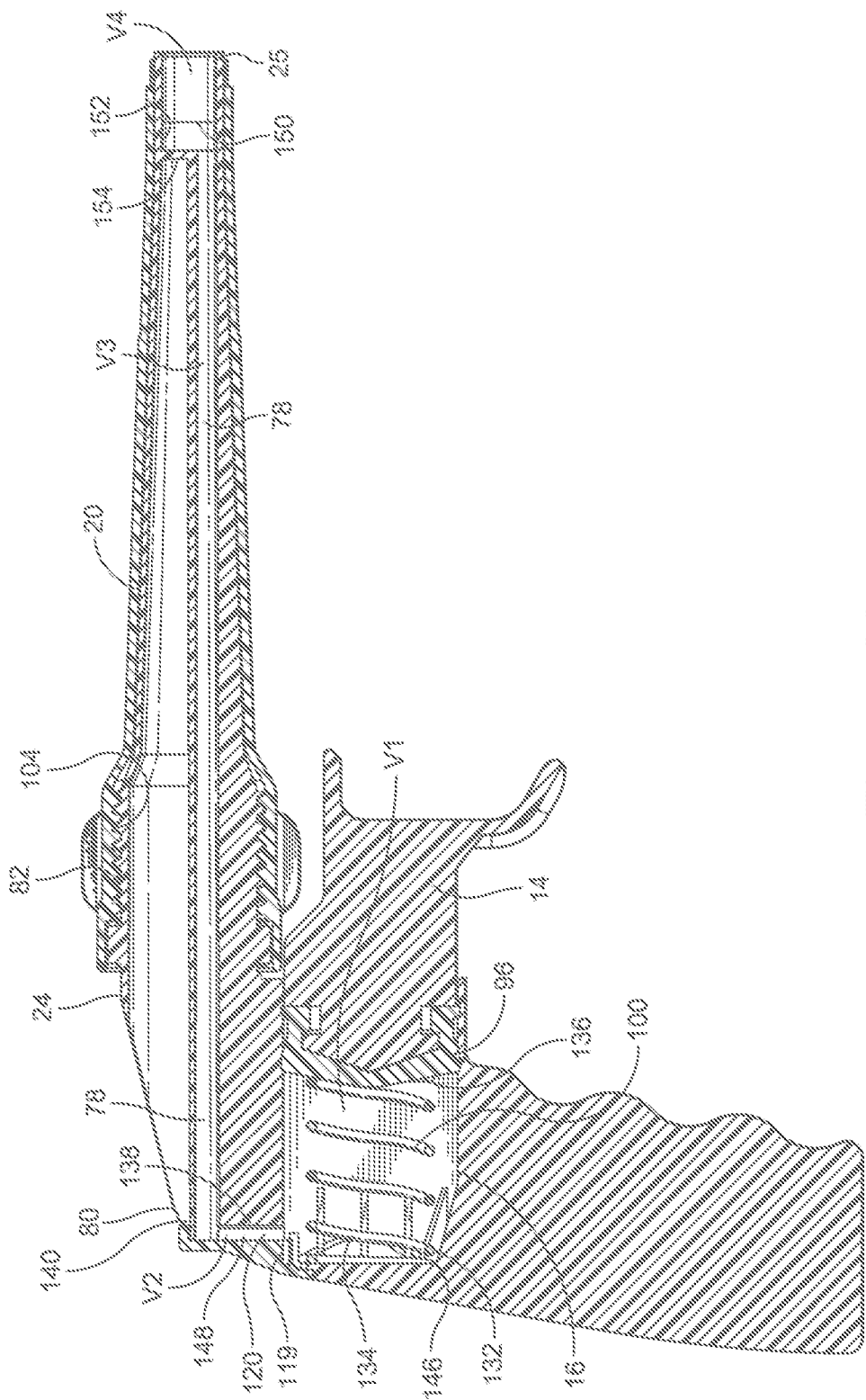
FIG. 22 is a cross-sectional view of the ligator of FIG. 1 taken through section line 22-22 of FIG. 4.

Referring next to FIG. 16, the back or plunging end 123 of the trigger 14 has a narrowed neck 123 intermediate a diametrally wider sealing cap base 125 and diametrally wider cap retainer/ram 127. With reference now to FIG. 22, the vacuum sealing cap 96 is somewhat C shaped to matingly surround and grip the cap retainer/ram 96 of the trigger 14. With reference to FIGS. 17-21, prior to being mounted to penetrate the vacuum drawing tube 16 as shown in FIG. 1, the vacuum sealing cap 96 is slightly wider than the width of the vacuum drawing tube 16. The sealing cap 96 thus provides a friction fit of the cap 96 within the vacuum drawing tube 16 and will sufficiently seal to allow drawing of a vacuum within the vacuum drawing tube 16 when the ligator, generally 10, as explained below.

With reference now to FIG. 22, the external banding barrel 24 is mounted on the fixed banding barrel 20 by threading the internal threaded section 104 of the external banding barrel 20 to mate with the external threaded section 82 on the fixed mounting barrel 20. An exemplary external threaded section is 20 mm wide, providing 6 fine threads, approximately 2 mm deep, along the length of fixed mounting barrel 20. The interior vacuum drawing barrel 78 extends from the back end 80 of the fixed banding barrel 20 to penetrate the diametrally wider band bearing tubular section or end 25 of the fixed banding barrel 20. The band bearing tubular section or end 25 has vacuum sealing wall 154 extending from around the periphery of the interior vacuum drawing barrel 78 to sealingly abut the surrounding interior periphery 152 of the fixed banding barrel 20. In some embodiments, the interior diameter of the band bearing tubular end 25 may be down to 1.50 inches. In some instances, the maximum interior diameter of forwardly tapering (i.e., somewhat conical, reducing in diameter from back to front end) vacuum drawing barrel 78 may be up to 1.30 inches.

The trigger 14 mounts within vacuum drawing tube 16 so that the vacuum sealing cap 96 is coaxial with both the axis of the vacuum drawing tube 16 and the axis of the spring 100. The spring 100 is intermediate, and respectively abuts at its opposing ends 130, 132, the vacuum sealing cap 96 and the concave rear wall 134 of the vacuum drawing tube 16. The concave rear wall 134 and slightly V-shaped or arced cross-section 136 of the vacuum sealing cap 96 cooperatively support the spring in position within the vacuum drawing tube 16.

Figure 23:
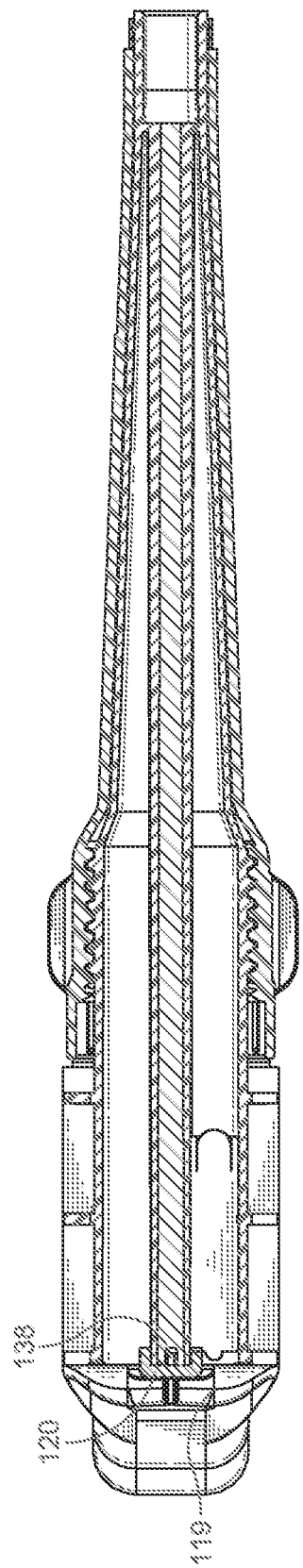
FIG. 23 is a cross-sectional view of the ligator of FIG. 1 taken along section line 23-23 of FIG. 2.

As shown in FIGS. 22 and 23, the sealing plug 120 is mounted in the plug mounting slot 119 spaced from air pathway channel 138 that extends upwardly from the back end 146 of the vacuum drawing tube 16 to the back end 140 of the vacuum drawing barrel 78. The sealing plug 120 and air pathway channel 138 thus cooperatively provide a sealed (vacuum drawing) air pathway 148 from the vacuum drawing tube 16 to the vacuum drawing barrel 78 and vice versa. With the trigger 14 in the uncompressed position (prior to compression of the spring 100), the volume V1 of the interior of the vacuum drawing tube 16 is 1.5 to 3 or more times the total volume V2+V3+V4 collectively provided by the air pathway 148, the vacuum drawing tube 16, and the vacuum drawing end 150 in the vacuum drawing barrel 20.

Referring back to FIG. 8, the fixed banding barrel 20, the interior vacuum drawing barrel 78, the vacuum drawing tube 16, and the handle 12 can be injection molded to form a one piece structure made of nearly transparent, rigid plastic, such as for example FDA-approved polyprophylene. This one piece structure can also be injection molded in two or more sections, which can then be formed into one piece by gluing or sonic welding the sections together. The trigger body 138, the sealing plug 120, and the external banding barrel 24 are also injection molded of nearly transparent plastic, such as FDA-approved polyethylene.

When assembled, the axis of each of the fixed banding barrel 20, the interior vacuum drawing barrel 78, and the vacuum drawing tube 16 are parallel and coplanar. In addition, the center axis of each of the fixed banding barrel 20 and the external banding barrel 24 are coaxial.

Referring back to FIG. 3, the resulting ligator can have the following dimensions shown in the Figures. Such a ligator can be extremely strong, economical, durable, and lightweight, weighing only 0.23 ounces when the components are made of polyethylene, rubber, and stainless steal as described above. The dimensions can and weight vary by anywhere from up to plus or minus 50%, or to as small or as large as may be needed for a given application.

Referring to the Figures generally, the ligator 10 can be used to attach a ligature or ligating band to human or other types of tissues. The ligator 10 can thus be used to place a ligating band on one or more hemorrhoids as follows:

1. Place one or more ligating bands on the band bearing tubular end 25 of the ligator 10.
2. Lubricate and place an anoscope, such as an off-the-shelf Anospec anooscope made by OBP Medical, Inc., of Lawrence, Mass., into the anus to detect hemorrhoidal tissue. This particular anoscope includes a minauture light source that directs light through the anoscope, including through its open smaller, penetrating end, providing the operator with the ability to observe an illuminated hemorrhoid and other tissue visible through that smaller end as well as through the nearly transparent anoscope side walls.
3. Grasp the ligator 10 as if it were a gun, placing the index finger on or adjacent the trigger 14 and the three other fingers in the mating finger grip channels 34, 36, 38.
4. While continuing to grasp the ligator with one hand:
   A. with the index finger, squeeze the trigger 14 so that it penetrates the vacuum drawing tube 16, forcing air out of the vacuum drawing tube 16, through the air pathway 148, through the vacuum drawing barrel 78, and out the tubular end 25 of the ligator 10;
   B. insert the band bearing tubular end 25 through the anoscope toward the hemorrhoid;
   C. look through the interior of the fixed banding tube 20 to observe the hemorrhoid and, while doing so, (i) position the band bearing tubular end 25 to surround the hemorrhoid and (ii) release squezzing pressure on the trigger 14 so that the stainless steel spring urges the trigger 14 outwardly from the vacuum drawing tube 16, drawing a vacuum in the tubular end 25 and sucking the entire hemorrhoid and possibly some supporting tissue into the tubular end 25;
   D. observe the hemorrhoid pulled by the resulting vacuum pressure within the band bearing tubular end 25 so that the end 25 surrounds the hemorrhoid;
   E. place the tip of the index finger on a finger tab near to top side of the ligator 10, e.g., 56; and
   F. with the tip of the index finger, if the finger tip is the right hand index finger tip, apply downwardly rotating pressure on the finger tab 56 (if the left hand finger tip, apply upwardly rotating pressure on the finger tab), causing the external banding barrel 24 to controllably rotate and thereby move toward and over the band bearing end 25, forcing a ligature over the band bearing end 25 to compress around the base of the hemorroid and any other tissue within the band bearing end 25. In the disclosed embodiment, the external banding barrel rotation is controlled by the interaction of inwardly extending adjuster tabs, e.g., 110, 112, and mating outwardly extending adjuster tabs, e.g., 114, 116. When these differing inwardly and outwardly extending adjuster tabs collide, they resist further rotation of the external banding barrel 24 with respect to the fixed vacuum drawing barrel 20 until the operator applies sufficient additional force to a finger tab 56, resulting in a clicking sound and feel to the operator as two interacting tabs separate and the barrel 24 rotates to the next tab stop brought about by interaction of a differing pair of mating such inwardly and outwardly extending adjuster tabs. The operator thus can carefully control the degree of rotation, and resulting lateral movement, of the external banding barrel 25 and, in turn, ligature movement along and off of the external banding barrel 25.
5. Either (i) move the anoscope to surround another hemorrhoid within the patient and repeat step 4; or (ii) remove the anoscope and ligator 10 from the patient.
6. Repeat step 5 as needed.

Each ligated tissue thereby loses its blood supply, dies, and is naturally excreted out of the patient, along with the ligature, typically within 5-7 days. In addition, in the event that steps 4C and 4D above result in an undesired amount of tissue being sucked into the band bearing tubular end, the position of the anoscope and/or ligator can be adjusted as desired and steps 4C and 4D repeated thereby acquiring the proper amount of hemorrhoidal tissue to be ligated. The ability to view suctioned material without an endoscope is a unique aspect of this device. Applicant believes that in all other devices, if an insufficient amount of tissue is suctioned and banded, it can be difficult to take corrective action.

The procedure described above is easy and quick, while being less intimidating to users and patients, less intrusive, and less risky than many prior art devices and techniques. This procedure typically requires 1-2 minutes to complete. The amount of patient discomfort is correspondingly reduced. In addition, this type of ligator and procedure can readily be used in an ambulatory setting because no external suctioning system is necessary in the embodiments shown in the Figures. The ligator's incorporated light source eliminates the need for a separate light system, such as a headlamp, thus reducing possible bacterial contamination of the separate light source.

The ligator 10 can be very economical to make, assemble, package, and ship. It can be disposed of after a single use, or it can be sanitized and re-used, particularly if it is made of metal, if desired. Further, the ligator 10 is dominantly made of recyclable polypropylene and steel, so the ligator 10 has minimal negative environmental impact when recycled or reused, depending on the material used.

The ligator 10 may also be made and supplied to users without ligating bands preloaded on the ligator 10; and in this fashion users can load conventional, off-the-shelf hemorrhoidal rubber bands on the ligator 10 with a conventional hemorrhoidal band loader. This can dramatically increase the shelf life of the ligator by three years or more.

With reference to FIG. 24, the ligator 10 can include an associated light source, such as a small battery and battery powered LED light source 170 mounted laterally to the side of, and abutting laterally, the back end 172 of the interior vacuum drawing barrel 78. The battery powered LED source 170 can be made removable by including a removable cover (not shown) covering and securing the battery and LED light source within the interior periphery of the fixed banding barrel 16. An exemplary such battery and LED source is a Zweibruder TT7830CP Micro Light. Alternatively, a light source can include use of (i) an optical cable to deliver light to a portion of the ligator 10, such as the band bearing end 25 or (ii) one or more flourescent light sources mounted to direct light toward the band bearing end 25.

Figure 14:
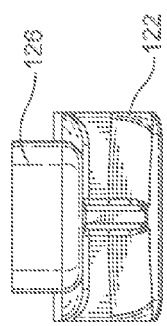
FIG. 14 is a top plan view of the plug of FIG. 8.
Figure 11:
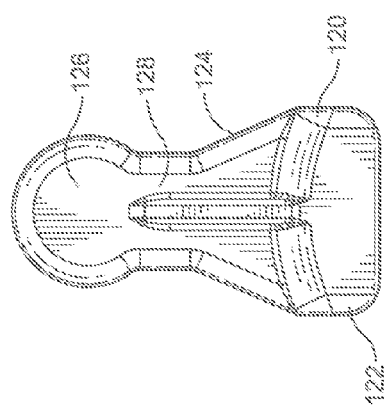
FIG. 11 is a rear elevational view of the plug of FIG. 8.
Figure 15:
FIG. 15 is a bottom plan view of the plug of FIG. 8.
Figure 12:
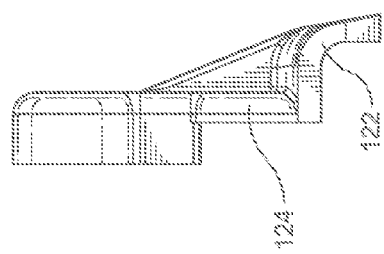
FIG. 12 is a left side elevational view of the plug of FIG. 8.

An embodiment of the ligator can include a magnifying lens in the viewing path of the user of the ligator. With reference to FIG. 14 for example, the sealing plug 120 can include a magnifying lens in or mounted to the sealing cap portion 126 of the sealing plug 120.

Referring now to FIG. 8, an embodiment of the ligator can utilize a hand squeezable balloon-like device in place of, or as an addition to, the vacuum drawing tube 12. In addition, other spring or trigger biasing mechanisms can be used in the place of, or in addition to, the stainless steel spring 100; and the trigger biasing mechanism can be deleted altogether, relying on the user to move the spring outwardly of the vacuum drawing tube 16.

Alternatively, a separate vacuum drawing structure could be use in addition to, or in place of, the vacuum drawing tube 16, trigger 14, and spring 100. For example, a vacuum drawing tube from a separate vacuum drawing device could be made connectable to the internal vacuum drawing barrel 78.

The trigger and handle can be made in variety of differing shapes other than those described above. For example, both the trigger and handle could utilize less material by being constructed differently, such as with thinner or less wide or deep portions.

Alternative uses of the present ligators or aspects of one or more of them include:
 banding of esophageal varices;
 laparoscopic surgery;
 veterinary use for animal sterilization, castration, and other procedures; and
 industrial or other uses for compression or other band deployment.

This description is not to be construed as limiting. Further, various components of embodiments disclosed herein may be mixed and matched with each other to yield further arrangements of the features disclosed herein.

The invention claimed is:

1. A hand-holdable ligator apparatus configured to ligate tissue, the apparatus comprising:
 a rigid elongate body having a proximal end and a distal end, the distal end configured to hold a ligating band thereon;
 a rigid vacuum draw tube extending within the rigid elongate body from the proximal end to the distal end along a straight first axis;
 a rigid viewing tube separate from the vacuum draw section and extending within the rigid elongate body from the proximal end to the distal end along a straight second axis that is parallel with the first axis, the rigid viewing tube having a translucent or transparent distal section configured to allow visualization of the tissue from the proximal end of the rigid elongate body;
 a ligating band actuator slidably mounted about the elongate body and configured to release the ligating band from the distal end of the rigid elongate body;
 a hand-holdable handle attached to the elongate body; and
 a vacuum actuator trigger attached to the hand-holdable handle, the trigger including a spring configured to compress to remove air from the vacuum section and to release to provide suction through the vacuum draw section to suction the tissue to the distal end of the rigid elongate body.

2. The hand-holdable ligator apparatus of claim 1, wherein the ligating band actuator includes a band actuator barrel rotatably mounted about the rigid elongate body, the band actuator barrel configured to rotate with respect to the rigid elongate body to cause axial movement of the band actuator barrel relative to the rigid elongate body to release the ligating band from the rigid elongate body.

3. The hand-holdable ligator of claim 2 wherein band actuator barrel is threadably mounted about the rigid elongate body.

4. The hand-holdable ligator of claim 2, wherein the band actuator barrel has a plurality of radially outwardly extending finger actuators.

5. The hand-holdable ligator apparatus of claim 1 wherein the vacuum actuator trigger includes a vacuum drawing chamber and a finger trigger including an air plunger section slidably mounted within the vacuum drawing chamber.

6. The hand-holdable ligator of claim 1, wherein the ligating band actuator comprises a finger actuator.

7. The hand-holdable ligator of claim 1 wherein the rigid viewing tube comprises translucent plastic.

8. The hand-holdable ligator of claim 1 wherein the rigid elongate body comprises translucent plastic.

9. The hand-holdable ligator of claim 1 wherein the hand-holdable ligator is comprised of rigid plastic.

10. The hand-holdable ligator of claim 1 further comprising a light source aimed at the distal end.

11. The hand-holdable ligator of claim 1, wherein the vacuum actuator trigger includes an air forcing plunger configured to slide into the vacuum draw section.

12. A unitary single-hand-holdable and -actuable ligator apparatus configured to ligate tissue, the apparatus comprising:
- a ligating barrel having a proximal end and a distal end, the distal end having a ligature mounting section configured to hold a ligating band thereon;
- a handle attached to the ligating barrel, the handle configured to be held by a hand;
- a vacuum actuation tube within the ligating barrel;
- a trigger attached to the handle, the trigger including a spring configured to compress to remove air from the vacuum actuation tube and to release to provide suction through the vacuum actuation tube, the trigger configured to be compressed and released by a single finger of the hand to provide suction through the vacuum actuation tube to suction the tissue to the ligature mounting section; and
- a rotatable ligature actuator barrel threadably mounted about the ligating barrel, the rotatable ligature actuator barrel having an actuation structure configured to be activated by a single finger of the hand to rotate the ligature actuator barrel with respect to the ligating barrel to cause axial movement of the ligature actuator barrel relative to the ligating barrel to release the ligating band from the ligature mounting section.

13. The unitary single-hand-holdable and -actuable ligator of claim 12 wherein the ligating barrel includes a tissue viewing channel extending from the proximal end to the distal end.

14. The unitary single-hand-holdable and -actuable ligator of claim 13 wherein the vacuum actuation tube is separate from the viewing channel.

15. The unitary single-hand-holdable and -actuable ligator of claim 12 wherein the ligature actuator barrel includes a plurality of rotatable finger tabs.

16. The unitary single-hand-holdable and -actuable ligator of claim 12 further comprising a light source directed toward the distal end of the ligating barrel.

17. The unitary single-hand-holdable and -actuable ligator of claim 12 wherein the trigger is biased outwardly from at least a portion of the vacuum actuation section.

* * * * *